(12) United States Patent
Han et al.

(10) Patent No.: US 9,873,811 B2
(45) Date of Patent: *Jan. 23, 2018

(54) HIGHLY CONDUCTIVE MATERIAL FORMED BY HYBRIDIZATION OF METAL NANOMATERIAL AND CARBON NANOMATERIAL HAVING HIGHER-ORDER STRUCTURE DUE TO MULTIPLE HYDROGEN BONDING, AND MANUFACTURING METHOD THEREFOR

(71) Applicant: KOREA ELECTROTECHNOLOGY RESEARCH INSTITUTE, Changwon-si, Gyeongsangnam-do (KR)

(72) Inventors: Joong-tark Han, Changwon-si (KR); Geon-woong Lee, Changwon-si (KR); Kang-jun Baeg, Changwon-si (KR); Bo-hwa Jeong, Busan (KR); Seung-yol Jeong, Gimhae-si (KR); Hee-jin Jeong, Changwon-si (KR)

(73) Assignee: Korea Electrotechnology Research Institute (KR)

(*) Notice: Subject to any disclaimer, the term of this patent is extended or adjusted under 35 U.S.C. 154(b) by 21 days.

This patent is subject to a terminal disclaimer.

(21) Appl. No.: 14/865,298

(22) Filed: Sep. 25, 2015

(65) Prior Publication Data
US 2016/0009934 A1 Jan. 14, 2016

Related U.S. Application Data

(63) Continuation of application No. PCT/KR2013/005190, filed on Jun. 12, 2013.

(30) Foreign Application Priority Data

Apr. 1, 2013 (KR) ........................ 10-2013-0035281

(51) Int. Cl.
| | |
|---|---|
| C09D 11/52 | (2014.01) |
| H01B 1/04 | (2006.01) |
| H01B 1/24 | (2006.01) |
| C07D 239/47 | (2006.01) |
| C09D 5/24 | (2006.01) |
| C09K 5/14 | (2006.01) |
| H01B 1/12 | (2006.01) |
| H01B 1/20 | (2006.01) |
| H05K 9/00 | (2006.01) |
| B82Y 30/00 | (2011.01) |

(52) U.S. Cl.
CPC ............. *C09D 11/52* (2013.01); *C07D 239/47* (2013.01); *C09D 5/24* (2013.01); *C09K 5/14* (2013.01); *H01B 1/04* (2013.01); *H01B 1/12* (2013.01); *H01B 1/20* (2013.01); *H01B 1/24* (2013.01); *H05K 9/009* (2013.01); *B82Y 30/00* (2013.01)

(58) Field of Classification Search
CPC ........ C09D 11/52; C09D 5/24; C07D 239/47; C09K 5/14; H01B 1/04; H01B 1/12; H01B 1/20; H01B 1/24; H05K 9/009; B82Y 30/00
USPC ........................................................ 428/402
See application file for complete search history.

(56) References Cited

U.S. PATENT DOCUMENTS

| | | | | |
|---|---|---|---|---|
| 9,227,941 | B2 * | 1/2016 | Han ................... | C01B 31/0273 |
| 9,277,941 | B2 * | 3/2016 | Biedermann ...... | A61B 17/7037 |
| 2008/0287638 | A1 * | 11/2008 | Reynolds ............. | B29C 73/163 |
| | | | | 528/59 |
| 2010/0112276 | A1 * | 5/2010 | Tsiper ................... | B82Y 30/00 |
| | | | | 428/114 |

FOREIGN PATENT DOCUMENTS

| | | | |
|---|---|---|---|
| KR | 10-2009-0032604 | * | 4/2009 |
| KR | 10-2009-0032604 A | | 4/2009 |
| KR | 10-2011-0095660 | * | 8/2011 |
| KR | 10-2011-0095660 A | | 8/2011 |
| KR | 10-1182380 | * | 9/2012 |

OTHER PUBLICATIONS

Feng, K et al., Photoinduced Triplet-Triplet Energy Transfer in a 2-Ureido-4(1H)-Pyrimidinone-Bridged, Quadruply Hydrogen-Bonded Ferrocene-Fullerene Assembly. Chemphyschem: a European journal of chemical physics and physical chemistry. 2013, vol. 14, No. 1, pp. 198-203, Published online on Nov. 30, 2012.
WIPO, International Search Report (PCT/KR2013/005190), dated Aug. 5, 2013.

* cited by examiner

*Primary Examiner* — Leszek Kiliman
(74) *Attorney, Agent, or Firm* — Park & Associates IP Law, P.C.

(57) ABSTRACT

The present invention relates to a highly conductive material formed by hybridization of a metal nanomaterial and a carbon nanomaterial having a higher-order structure due to multiple hydrogen bonding, and to a manufacturing method therefor. The technical essence of the present invention is a highly conductive material formed by hybridization of a metal nanomaterial and a carbon nanomaterial having a higher-order structure due to multiple hydrogen bonding the invention involving: forming a carbon nanomaterial having a higher-order structure due to multiple hydrogen bonding between conductive carbon nanomaterials by introducing a functional group capable of multiple hydrogen bonding to the carbon nanomaterials; forming a composite material by mixing the carbon nanomaterial having a higher-order structure and a metal nanomaterial.

20 Claims, 4 Drawing Sheets

(a) 
highly concentrated dispersion paste (b) 
diluted solution

`US 9,873,811 B2`

HIGHLY CONDUCTIVE MATERIAL FORMED BY HYBRIDIZATION OF METAL NANOMATERIAL AND CARBON NANOMATERIAL HAVING HIGHER-ORDER STRUCTURE DUE TO MULTIPLE HYDROGEN BONDING, AND MANUFACTURING METHOD THEREFOR

REFERENCE TO RELATED APPLICATIONS

This is a continuation of pending International Patent Application PCT/KR2013/005190 filed on Jun. 12, 2013, which designates the United States and claims priority of Korean Patent Application No. 10-2013-0035281 filed on Apr. 1, 2013, the entire contents of which are incorporated herein by reference.

FIELD OF THE INVENTION

The present invention relates to a highly conductive material formed by hybridization between a carbon nanomaterial having a higher-order structure based on multiple hydrogen bonding and a metal nanomaterial, and a method for manufacturing the same. More particularly, the present invention relates to a highly conductive material, prepared from a hybrid of a carbon nanomaterial having a higher-order structure based on multiple hydrogen bonding and a metal nanomaterial, wherein the conductive carbon nanomaterial, such as a carbon nanotube, graphene, a carbon fiber, carbon black, etc., is grafted with a functional group capable of three or more hydrogen bonds so as to afford a supermolecular carbon nanomaterial having a higher-order structure based on multiple hydrogen bonding, and is complexed with a highly conductive metal nanomaterial, such as a silver nanowire, copper nanowire, etc., and a method for manufacturing the same.

BACKGROUND OF THE INVENTION

On the whole, conductive carbon nanomaterials, such as carbon nanotubes, graphene, carbon fibers, carbon black and so forth, find applications in a variety of fields including transparent electrodes, antistatic finishing, electromagnetic wave shielding, electrodes for energy generation and energy storage devices, heat dissipation materials, conductive fibers, sensors, emitters, X-ray light sources, etc. For use in forming an electrode by use of a printing technique or in preparing fibers, a highly concentrated dispersion or spinning dope of conductive nanomaterials in a paste form is needed. Application of such conductive carbon nanomaterials to transparent electrodes requires a relatively dilute coating solution of the carbon nanomaterials that exhibits superior dispersibility.

In this regard, a surfactant or a dispersant, such as a copolymer, ionic liquid, etc., is requisite for preparing a coating solution or paste of conductive nanomaterials. Of course, when excessive functional groups are introduced onto the surface thereof, conductive materials can be easily dispersed, but lose their conductivity.

Further, the electroconductivity of carbon nanomaterials can be extremely increased when even a small amount of a metal nanomaterial having a one- or two-dimensional structure is added thereto. However, only when the carbon nanomaterial in mixture with the metal nanomaterial keeps its dispersibility high, can it be applied to transparent electrodes, conductive fibers, energy electrodes, etc.

Therefore, if a conductive nanomaterial-based paste keeps high dispersibility without using a dispersant, hybridization of the conductive nanomaterial-based paste with a metal nanomaterial brings about an improvement in conductivity, production cost and process simplification as well as allowing for substitution for conventional electrode materials. Given, a carbon nanomaterial/metal nanomaterial hybrid that is able to disperse in an organic solvent even in the absence of an aqueous dispersant further has the advantage of enabling combination with various materials that are feasibly compatible to an organic solvent, including polymer binder materials, metals, and metal oxides.

However, thus far nowhere has the preparation of a coating solution based on the hybridization of a carbon nanomaterial with a metal nanomaterial without using a dispersant been reported.

SUMMARY OF THE INVENTION

Accordingly, the present invention has been made keeping in mind the above problems occurring in the prior art, and an object of the present invention is to provide a highly conductive material, prepared from a hybrid of a carbon nanomaterial having a higher-order structure based on multiple hydrogen bonding and a metal nanomaterial, wherein the conductive carbon nanomaterial, such as a carbon nanotube, graphene, a carbon fiber, carbon black, etc., is grafted with a functional group capable of three or more hydrogen bonds so as to afford a supermolecular carbon nanomaterial having a higher-order structure based on multiple hydrogen bonding, and is complexed with a highly conductive metal nanomaterial, such as a silver nanowire, copper nanowire, etc., and a method for manufacturing the same.

In order to accomplish the above object, an aspect of the present invention provides a highly conductive material, prepared by mixing a conductive carbon nanomaterial having a higher-order structure based on multiple hydrogen bonding and a metal nanomaterial to give a composite material, the conductive carbon nanomaterial being grafted with a functional group capable of forming multiple hydrogen bonds.

Another aspect of the present invention provides a method for manufacturing a highly conductive material, comprising steps of: (1) modifying a surface of a carbon nanomaterial to make it feasible to introduce a functional group capable of forming multiple hydrogen bonds onto the surface; (2) grafting the modified carbon nanomaterial with the functional group capable of forming multiple hydrogen bonds; and (3) mixing the functional group-grafted carbon nanomaterial of step (2) with a metal nanomaterial to form a composite material in a dispersion solution form.

In one exemplary embodiment of the present invention, the carbon nanomaterial is at least one of a carbon nanotube, a carbon fiber, graphene, and carbon black.

In another exemplary embodiment of the present invention, the metal nanomaterial is at least one of a one-dimensional metal nanowire, a one-dimensional nanorod, and a two-dimensional platy metal nanomaterial.

In another exemplary embodiment of the present invention, the functional group capable of forming multiple hydrogen bonds is at least one of a 2-ureido-4[1H]pyrimidinone) derivative, a 4-ureido-4[1H]pyrimidinol) derivative, a 2-uriedo-4-pyrimidone derivative, a diacylpyrimidine derivative, a ureidoacylpyrimidine derivative, an acetylaminotriazine derivative, an ureidotriazine derivative, a 2,6-di (acetylamino)-4-pyridyl derivative, a thymine derivative, a 2-aminobenzimidazole derivative, a 2,7-diamino-1,8-naphthyridine derivative, a di(hexanoylamino)pyrimidine derivative, and a 2-butylureido-4-acetylaminopyridine derivative.

In another exemplary embodiment of the present invention, the composite material is dispersed at a concentration of 0.01 g/L or higher in an aqueous solution or an organic solvent without using a dispersant.

In another exemplary embodiment of the present invention, the composite material is used in a transparent electrode, a printed electrode, a flexible electrode, a surface heater, an electrostatic discharge coating agent, an EMI (electromagnetic interference) shield coating agent, an ink paint, a conductive fiber, and a heat dissipation paint.

In another exemplary embodiment of the present invention, the transparent electrode, the printed electrode, the surface heater, the electrostatic discharge coating agent, the EMI (electromagnetic interference) shield coating agent, or the ink paint is prepared from a dilution of the composite material.

In another exemplary embodiment of the present invention, the flexible electrode is prepared by stirring the composite material in a solution or molten state of a rubber to give a dispersion, and printing or forming the dispersion.

In another exemplary embodiment of the present invention, the conductive fiber is prepared by mixing the composite material with a liquid resin for fibers to give a dispersion, and spinning the dispersion.

In another exemplary embodiment of the present invention, the heat dissipation paint is prepared by dispersing the composite material, together with a heat dissipation material, in a binder resin.

Accordingly, a conductive carbon nanomaterial, such as a carbon nanotube, graphene, a carbon fiber, carbon black, etc., is grafted with a functional group capable of three or more hydrogen bonds so as to afford a supermolecular carbon nanomaterial having a higher-order structure based on multiple hydrogen bonding, and the supermolecular carbon nanomaterial having a higher-order structure based on multiple hydrogen bonding can be complexed with a highly conductive metal nanomaterial, without using a dispersant, to prepare a highly conductive material that can find applications in various fields including electrodes of energy generation and storage devices such as solar cells, rechargeable batteries, fuel cells, supercapacitors, etc., and conductive fibers as well as transparent electrodes, printed electrodes, flexible electrodes, surface heaters, and electromagnetic wave shielding materials.

As described above, the highly conductive material of the present invention, prepared by grafting a conductive carbon nanomaterial, such as a carbon nanotube, a graphene, a carbon fiber, carbon black, etc., with a functional group capable of three or more hydrogen bonds so as to afford a supermolecular carbon nanomaterial having a higher-order structure based on multiple hydrogen bonding, and by complexing the supermolecular carbon nanomaterial having a higher-order structure based on multiple hydrogen bonding with a highly conductive metal nanomaterial, finds applications in various fields including electrodes of energy generation and storage devices such as solar cells, rechargeable batteries, fuel cells, supercapacitors, etc., and conductive fibers as well as transparent electrodes, printed electrodes, flexible electrodes, surface heaters, and electromagnetic wave shielding materials.

DETAILED DESCRIPTION OF THE INVENTION

Figure 1:
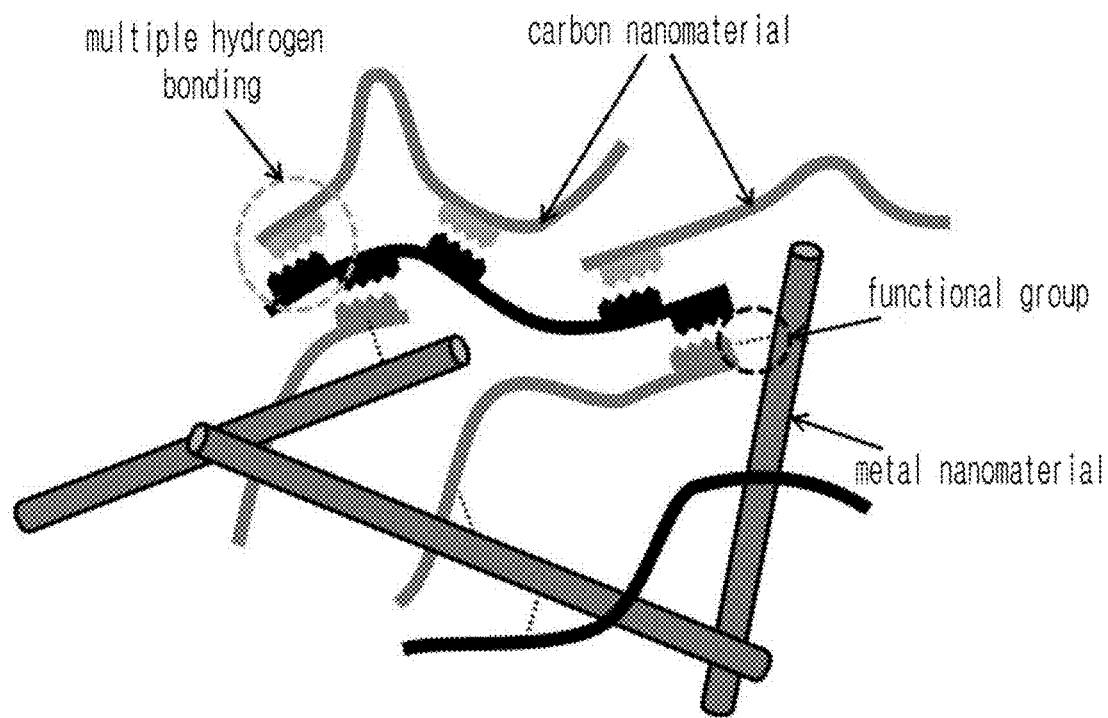
FIG. 1 is a schematic view illustrating a hybrid structure of a carbon nanomaterial having multiple hydrogen bonding and a metal nanomaterial in accordance with an exemplary embodiment of the present invention.

Reference should now be made to the drawings, in which the same reference numerals are used throughout the different drawings to designate the same or similar components.

Figure 2:
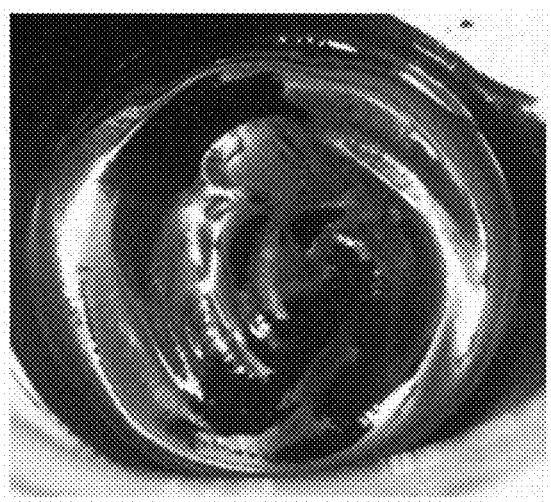
FIG. 2 shows photographic images of a paste and a dilute solution thereof, prepared according to an exemplary embodiment of the present invention.
Figure 2:
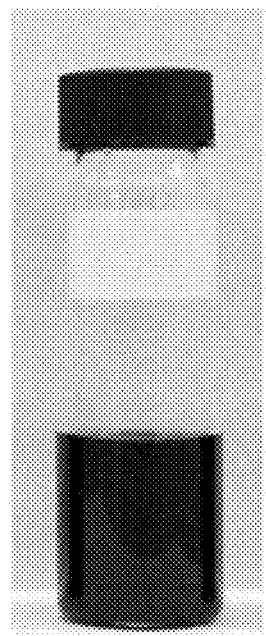
Figure 3:
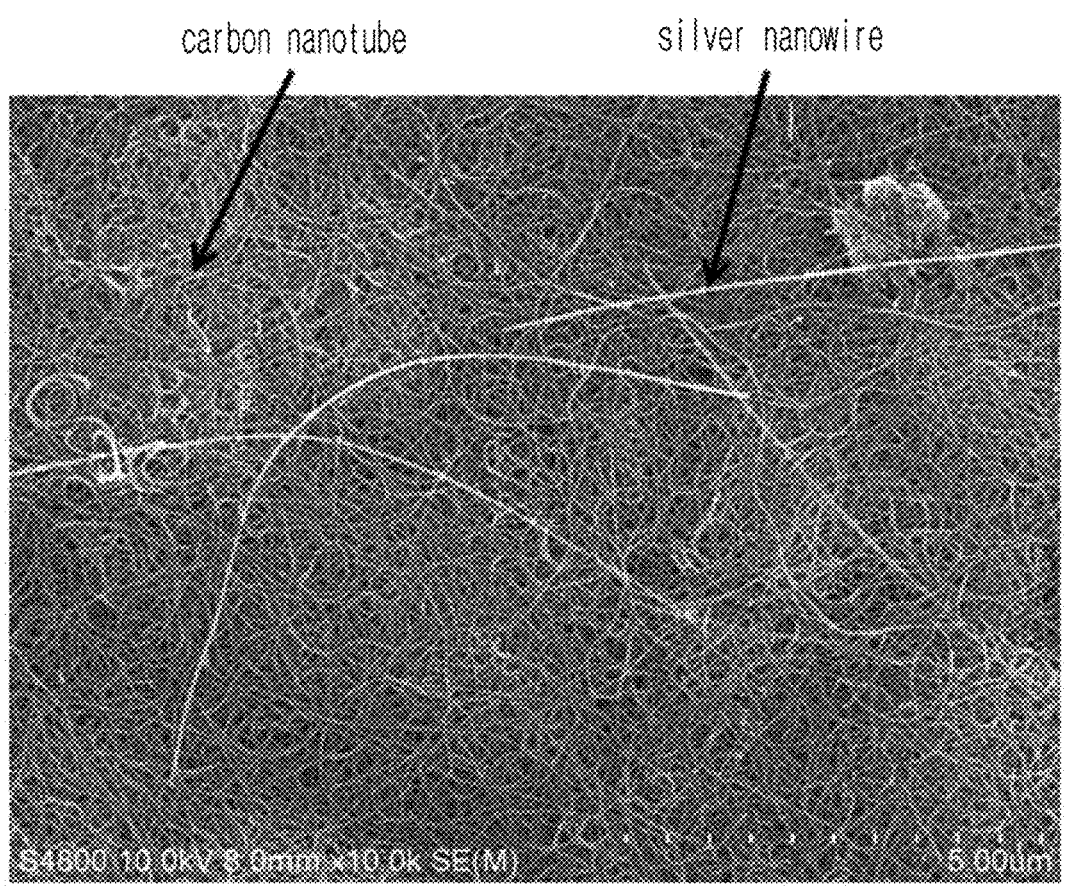
FIG. 3 is a scanning electron microscopic image of the surface of a composite electrode composed of a carbon nanotube having multiple hydrogen bonding and a silver nanowire in accordance with an exemplary embodiment of the present invention.
Figure 4:
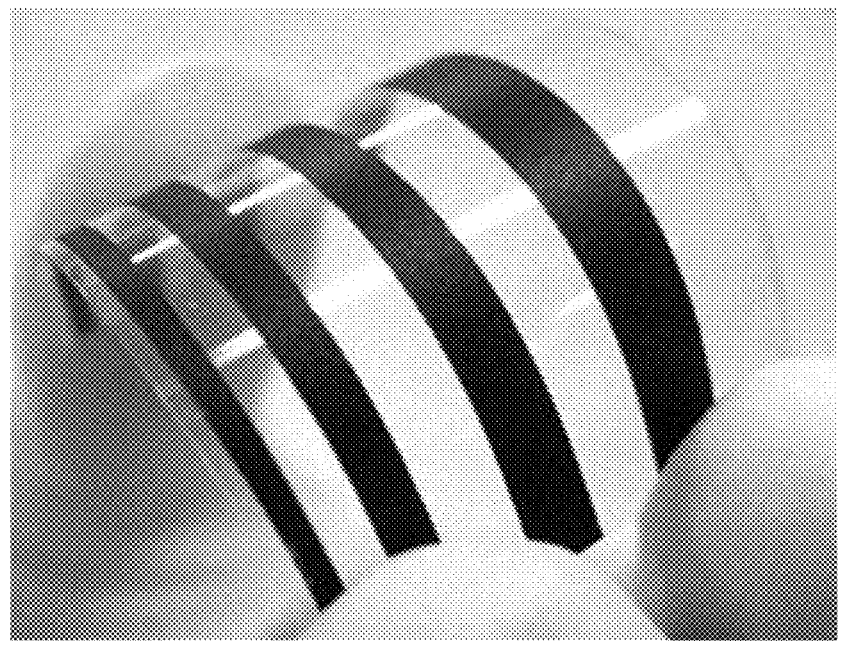
FIG. 4 is an image of a printed electrode prepared from a composite solution containing a carbon nanotube having multiple hydrogen bonding and a metal nanowire in accordance with an exemplary embodiment of the present invention.
Figure 5:
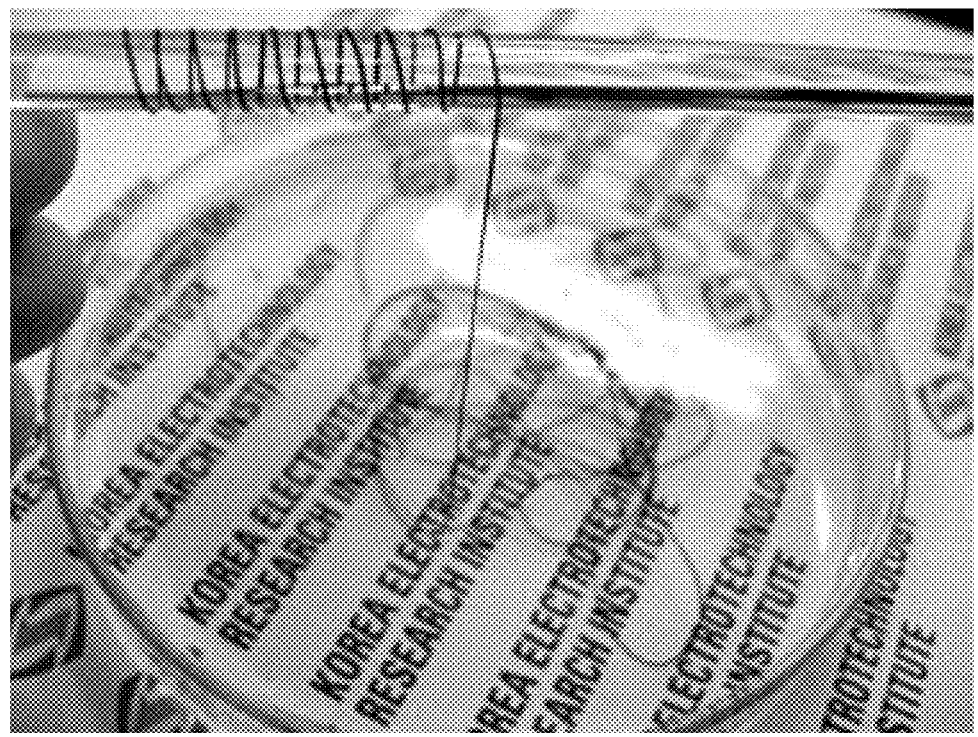
FIG. 5 is an image of a conductive fiber prepared from a composite solution containing a carbon nanotube having multiple hydrogen bonding and a metal nanowire in accordance with an exemplary embodiment of the present invention.
Figure 6:
FIG. 6 is an image of a transparent film prepared from a composite solution containing a carbon nanotube having multiple hydrogen bonding and a metal nanowire in accordance with an exemplary embodiment of the present invention.

FIG. 1 is a schematic view illustrating a hybrid structure of a carbon nanomaterial having multiple hydrogen bonding and a metal nanomaterial in accordance with an exemplary embodiment of the present invention. FIG. 2 shows photographic images of a paste and a dilute solution thereof, prepared according to an exemplary embodiment of the present invention. FIG. 3 is a scanning electron microscopic image of the surface of a composite electrode composed of a carbon nanotube having multiple hydrogen bonding and a silver nanowire in accordance with an exemplary embodiment of the present invention. FIG. 4 is an image of a printed electrode prepared from a composite solution containing a carbon nanotube having multiple hydrogen bonding and a metal nanowire in accordance with an exemplary embodiment of the present invention. FIG. 5 is an image of a conductive fiber prepared from a composite solution containing a carbon nanotube having multiple hydrogen bonding and a metal nanowire in accordance with an exemplary embodiment of the present invention. FIG. 6 is an image of a transparent film prepared from a composite solution containing a carbon nanotube having multiple hydrogen bonding and a metal nanowire in accordance with an exemplary embodiment of the present invention.

As can be seen in the drawings, an aspect of the present invention addresses a highly conductive material, prepared by hybridizing a carbon nanomaterial having a higher-order structure based on multiple hydrogen bonding and a metal nanomaterial. Also, contemplated in accordance with another aspect of the present invention is a method for manufacturing the highly conductive material, comprising: step 1 of modifying a surface of a carbon nanomaterial to make it feasible to introduce a functional group capable of forming multiple hydrogen bonds onto the surface; step 2 of grafting the modified carbon nanomaterial with the functional group capable of forming multiple hydrogen bonds;

and step 3 of mixing the functional group-grafted carbon nanomaterial of step 2 with a metal nanomaterial to form a composite material in a dispersion solution form. Below, a detailed description will be given of the highly conductive material and the method.

Multiple hydrogen bonds may be composed of a hydrogen bond donor (D), a hydrogen bond acceptor (A), and an ionic hydrogen bond donor (D+). For triple hydrogen bonding, D, D+, and A may be arranged in a pair form of ADA-DAD, ADD-DAA, AAA-DDD, or cationic AAA-DDD+. An arrangement of D, D+, and A for quadruple hydrogen bonding may be a pair structure selected from among ADAD-DADA, AADD-DDAA, ADDA-DAAD, AAAD-DDDA, ADAA-DADD, AAAA-DDDD, and cationic AAAA-DDDD+.

Examples of the functional group capable of forming multiple hydrogen bonds include a 2-ureido-4[1H]pyrimidinone derivative, a 4-ureido-4[1H]pyrimidinol derivative, a 2-uriedo-4-pyrimidone derivative, a diacylpyrimidine derivative, a ureidoacylpyrimidine derivative, an acetylaminotriazine derivative, an ureidotriazine derivative, a 2,6-di(acetylamino)-4-pyridyl derivative, a thymine derivative, a 2-aminobenzimidazole derivative, a 2,7-diamino-1,8-naphthyridine derivative, a di(hexanoylamino)pyrimidine derivative, a 2-butylureido-4-acetylaminopyridine derivative, and a combination thereof.

The metal nanomaterial may be selected from among a one-dimensional metal nanowire, a one-dimensional metal nanorod, a two-dimensional platy metal nanomaterial, and a combination thereof.

EXAMPLE 1

In Example 1, a multiwall carbon nanotube was grafted with a functional group capable of forming quadruple hydrogen bonds and hybridized with a silver nanowire.

First, 10 g of a multiwall carbon nanotube in 200 ml of sulfuric acid/nitric acid mixture (7:3 v/v) was heated at 80° C. for 24 hrs with stirring, and then cooled to room temperature.

Then, the mixture was diluted with 800 ml of distilled water. The dilution was filtered four or more times through filter paper to obtain a carboxyl group (—COOH)-grafted multiwall carbon nanotube while the acid was removed.

The carboxyl group (—COOH)-grafted carbon nanotube was dispersed at a concentration of 100 mg/L in a dimethylformamide solvent, and then grafted with isocyanate by mixing with a diisocyanate having a thiol (—SH) or amine group at 100° C. for 12 hrs while stirring.

Subsequently, the diisocyanate-grafted carbon nanotube was mixed at 100° C. for 20 hrs with amino-4-hydroxy-6-methyl-pyrimidine while stirring so as to introduce 2-ureido-4[1H]pyrimidinone into the carbon nanotube that was therefore capable of quadruple hydrogen bonding.

A structure of a composite comprising a carbon nanotube having multiple hydrogen bonding and a metal nanomaterial is schematically shown in FIG. 1.

The supermolecular carbon nanotube having multiple hydrogen bonding was simply stirred in a dimethylformamide solvent without using an additive to give a paste. This paste was added with various amounts of a dispersion of silver nanowires in distilled water without using particular additives while stirring to give carbon nanotube/silver nanowire composite pastes with a solid content of 1 wt % or higher. In FIG. 2, a paste with a solid content of 5 wt %, formed by adding 5 wt % of a silver nanowire to the carbon nanotube, is shown (a), and diluted 100-fold in distilled water (b). As such, a carbon nanotube/silver nanowire paste can be easily prepared by simply stirring.

As can be seen in FIG. 1, thiol or amine groups, and other groups in the functional group capable of forming multiple hydrogen bonds interact with the silver nanowire so that the silver nanowire can be stabilized with the carbon nanomaterial.

In addition, as can be seen in FIG. 3, the carbon nanotubes and the silver nanowires were uniformly dispersed.

Using a screen printing, gravure, slot die, or offset printing technique, the pastes were formed into flexible printed electrodes on a plastic substrate. The printed electrodes were evaluated for electrical properties. The multiwall carbon nanotube having a multiple hydrogen bonding functional group was found to increase in electroconductivity from 1,000 S/m to 10,000 S/m when a silver nanowire was added in an amount of 5 wt % thereto.

FIG. 4 is an image of a flexible printed electrode prepared from the paste of Example 1 by screen printing.

Far superior in electroconductivity, the printed electrode can be applied to general wire electrodes, solar cell electrodes, organic light emitting device electrodes, surface heaters, and EMI (Electromagnetic interference) shielding.

EXAMPLE 2

In Example 2, a conductive fiber was prepared a mixture of a carbon nanomaterial having a higher-order structure based on multiple hydrogen bonding, a metal nanowire, and a polymer.

Both a multiwall carbon nanotube and a chemically exfoliated graphene were grafted with a functional group capable of forming quadruple hydrogen bonds in the same manner as in Example 1, followed by mixing a silver nanowire in an amount of 3 wt % of the carbon nanomaterial to give a conductive paste with a solid content of 5 wt %.

The chemically exfoliated graphene was prepared by treating pure graphite with sulfuric acid $KMnO_4$ for 3 days, purifying with hydrogen peroxide and hydrochloric acid to give graphite oxide, and exfoliating the graphite oxide by use of an ultrasonic processor.

To the conductive paste, a solution of polyacrylonitrile in dimethylformamide was added in an amount of 50 wt % of the solid content of the conductive paste to give a dope for use in fiber spinning.

The dope was spun through a spinneret having a diameter of 100 μm into a conductive fiber with an electroconductivity of 100 S/cm.

FIG. 5 shows an image of the conductive fiber prepared in Example 2. As can be seen, the dope was well formed into fibers.

EXAMPLE 3

In Example 3, a transparent electrode was prepared from a highly conductive composite material. For this, first, a functional group capable of forming multiple hydrogen bonds was introduced into single-wall carbon nanotube in the same manner as in Example 1, and the carbon nanotube was mixed with a silver nanowire in a dimethylformamide to give a paste that was then diluted to a concentration of 0.01 wt %. The dilution was applied to a plastic or glass substrate using a spray coating or slot-die coating technique to form a transparent electrode.

FIG. 6 is an image of the flexible transparent conductive film formed on a plastic substrate as prepared in Example 3. The transparent conductive film was found to have a surface resistance of 50 ohm/sq, which was decreased to 10% or less of that of the single-wall carbon nanotube alone, and to exhibit a transmittance of 85%.

EXAMPLE 4

In Example 4, grapheme oxide was grafted with a functional group capable of forming multiple hydrogen bonds in the same manner as in Example 2, and stirred in N-methyl pyrrolidone to give a paste with a concentration of 10 wt %.

Briefly, graphene oxide, which is an electrical insulator, was converted into a conductive form by reduction with hydrazine at 100° C. for 24 hrs. The conductive graphene was grafted as mentioned above, and prepared into a paste that was then mixed with a copper nanowire to afford a hybrid conductive paste in which the graphene and the copper nanowire were uniformly dispersed.

The paste may be formed into a pattern electrode, as shown in FIG. 4, by a printing process, or into a conductive fiber by a solution spinning process. In addition, the paste may be diluted and formed into a transparent electrode as in Example 3. In this case, the graphene protects the copper nanowire while the copper nanowire prevents the re-association of the graphene. Accordingly, the transparent electrode is stable to moisture or external physical stimuli and shows high transmittance with a low surface resistance. Thus, it is applicable to touch panel electrodes, display electrodes, and solar cell electrodes as well as transparent surface heaters.

EXAMPLE 5

Preparation of Heat Dissipation Paint

A multiple hydrogen bond-bearing carbon nanomaterial (carbon nanotube, graphene, carbon fiber, carbon black, thin graphite) or a multiple hydrogen bond-bearing carbon nanomaterial/metal nanomaterial (silver nanowire, copper nanowire) composite was uniformly dispersed, together with a heat dissipation material (alumina, SiC, metal, nanodiamond, boron nitride, ZnS, magnetic substance, conductive polymer), in a binder resin to afford a heat dissipation paint.

EXAMPLE 6

Preparation of Flexible Electrode

A powder or dispersion of the multiple hydrogen bond-bearing carbon nanomaterial (carbon nanotube, graphene, carbon fiber, carbon black, thin graphite) or the multiple hydrogen bond-bearing carbon nanomaterial/metal nanomaterial (silver nanowire, copper nanowire) composite was dispersed in an amount of 1~30 wt % in a liquid phase or a molten state of a highly flexible rubber (vulcanized natural rubber, styrene-butadiene rubber, polystyrene-polyisoprene-polystyrene, polysiloxane fluoride copolymer, and a combination), and transformed into a flexible electrode that changed in electroconductivity within 10% by a casting, printing or forming technique.

As described hitherto, a highly conductive material, prepared from a hybrid of a carbon nanomaterial having a higher-order structure based on multiple hydrogen bonding and a metal nanomaterial, and a method for manufacturing the same are disclosed. A conductive carbon nanomaterial, such as a carbon nanotube, graphene, a carbon fiber, carbon black, etc., is grafted with a functional group capable of three or more hydrogen bonds so as to afford a supermolecular carbon nanomaterial having a higher-order structure based on multiple hydrogen bonding. This supermolecular carbon nanomaterial having a higher-order structure based on multiple hydrogen bonding is complexed with a highly conductive metal nanomaterial, such as a silver nanowire, copper nanowire, etc., to prepare a highly conductive material.

What is claimed is:

1. A nano carbon and metal hybrid material, prepared by mixing a conductive carbon nanomaterial having a higher-order structure based on multiple hydrogen bonding and a metal nanomaterial to give a composite material, the conductive carbon nanomaterial being grafted with a functional group capable of forming multiple hydrogen bonds.

2. The nano carbon and metal hybrid material of claim 1, wherein the carbon nanomaterial is at least one of a carbon nanotube, a carbon fiber, a graphene, and carbon black.

3. The nano carbon and metal hybrid material of claim 1, wherein the metal nanomaterial is at least one of a one-dimensional metal nanowire, a one-dimensional nanorod, and a two-dimensional platy metal nanomaterial.

4. The nano carbon and metal hybrid material of claim 1, wherein the functional group capable of forming multiple hydrogen bonds is at least one of a 2-ureido-4[1H]pyrimidinone) derivative, a 4-ureido-4[1H]pyrimidinol) derivative, a 2-uriedo-4-pyrimidone derivative, a diacylpyrimidine derivative, a ureidoacylpyrimidine derivative, an acetylaminotriazine derivative, an ureidotriazine derivative, a 2,6-di(acetylamino)-4-pyridyl derivative, a thymine derivative, a 2-aminobenzimidazole derivative, a 2,7-diamino-1,8-naphthyridine derivative, a di(hexanoylamino)pyrimidine derivative, and a 2-butylureido-4-acetylaminopyridine derivative.

5. The nano carbon and metal hybrid material of claim 1, wherein the composite material is dispersed at a concentration of 0.01 g/L or higher in an aqueous solution or an organic solvent without using a dispersant.

6. The nano carbon and metal hybrid material of claim 1, wherein the composite material is used in a transparent electrode, a printed electrode, a flexible electrode, a surface heater, an electrostatic discharge coating agent, an EMI (electromagnetic interference) shield coating agent, an ink paint, a conductive fiber, and a heat dissipation paint.

7. The nano carbon and metal hybrid material of claim 6, wherein the transparent electrode, the printed electrode, the surface heater, the electrostatic discharge coating agent, the EMI (electromagnetic interference) shield coating agent, or the ink paint is prepared from a dilution of the composite material.

8. The nano carbon and metal hybrid material of claim 6, wherein the flexible electrode is prepared by stirring the composite material in a solution or molten state of a rubber to give a dispersion, and printing or forming the dispersion.

9. The nano carbon and metal hybrid material of claim 6, wherein the conductive fiber is prepared by mixing the composite material with a liquid resin for fibers to give a dispersion, and spinning the dispersion.

10. The nano carbon and metal hybrid material of claim 6, wherein the heat dissipation paint is prepared by dispersing the composite material, together with a heat dissipation material, in a binder resin.

11. A method for manufacturing a nano carbon and metal hybrid material, comprising steps of:
(1) modifying a surface of a carbon nanomaterial to make it feasible to introduce a functional group capable of forming multiple hydrogen bonds onto the surface;

(2) grafting the modified carbon nanomaterial with the functional group capable of forming multiple hydrogen bonds; and (3) mixing the functional group-grafted carbon nanomaterial of step (2) with a metal nanomaterial to form a composite material in a dispersion solution form.

12. The method of claim 11, wherein the carbon nanomaterial is at least one of a carbon nanotube, a carbon fiber, a graphene, and carbon black.

13. The method of claim 11, wherein the metal nanomaterial is at least one of a one-dimensional metal nanowire, a one-dimensional nanorod, and a two-dimensional platy metal nanomaterial.

14. The method of claim 11, wherein the functional group capable of forming multiple hydrogen bonds is at least one of a 2-ureido-4[1H]pyrimidinone) derivative, a 4-ureido-4 [1H]pyrimidinol) derivative, a 2-uriedo-4-pyrimidone derivative, a diacylpyri midi ne derivative, a ureidoacyl pyri midi ne derivative, an acetylaminotriazine derivative, an ureidotriazine derivative, a 2,6-di(acetylamino)-4-pyridyl derivative, a thymine derivative, a 2-aminobenzimidazole derivative, a 2,7-diamino-1,8-naphthyridine derivative, a di(hexanoylamino)pyrimidine derivative, and a 2-butylureido-4-acetylaminopyridine derivative.

15. The method of claim 11, wherein the composite material is dispersed at a concentration of 0.01 g/L or higher in an aqueous solution or an organic solvent without using a dispersant.

16. The method of claim 11, wherein the composite material is used in a transparent electrode, a printed electrode, a flexible electrode, a surface heater, an electrostatic discharge coating agent, an EMI (electromagnetic interference) shield coating agent, an ink paint, a conductive fiber, and a heat dissipation paint.

17. The method of claim 16, wherein the transparent electrode, the printed electrode, the surface heater, the electrostatic discharge coating agent, the EMI (electromagnetic interference) shield coating agent, or the ink paint is prepared from a dilution of the composite material.

18. The method of claim 16, wherein the flexible electrode is prepared by stirring the composite material in a solution or molten state of a rubber to give a dispersion, and printing or forming the dispersion.

19. The method of claim 16, wherein the conductive fiber is prepared by mixing the composite material with a liquid resin for fibers to give a dispersion, and spinning the dispersion.

20. The method of claim 16, wherein the heat dissipation paint is prepared by dispersing the composite material, together with a heat dissipation material, in a binder resin.

* * * * *